United States Patent [19]

Seko

[11] Patent Number: 5,466,871
[45] Date of Patent: Nov. 14, 1995

[54] PROCESS FOR PREPARING NITROANILINE DERIVATIVES

[75] Inventor: Shinzo Seko, Osaka, Japan

[73] Assignee: Sumitomo Chemical Company, Limited, Osaka, Japan

[21] Appl. No.: 272,847

[22] Filed: Jul. 11, 1994

[30] Foreign Application Priority Data

| Jul. 22, 1993 | [JP] | Japan | 5-181637 |
| Nov. 24, 1993 | [JP] | Japan | 5-293056 |
| Dec. 10, 1993 | [JP] | Japan | 5-310285 |
| Mar. 7, 1994 | [JP] | Japan | 6-035831 |
| Mar. 7, 1994 | [JP] | Japan | 6-035834 |

[51] Int. Cl.$^6$ .................................................. C07C 209/02
[52] U.S. Cl. .................. 564/395; 564/399; 564/406; 564/407; 564/440; 564/441; 564/467
[58] Field of Search ......................... 564/395, 399, 564/406, 407, 440, 441, 393; 549/467

[56] References Cited

U.S. PATENT DOCUMENTS

5,120,853  6/1992  Yoneyoshi et al. ................ 548/268.4

OTHER PUBLICATIONS

Houben Weyl "Methoden der organischen . . . 4th ed., vol. XI/1 Stickstoffverbindungen" 1957, pp. 17–19.
Chem. Abs., vol. 77, No. 9, 1972, Aug. 28, Ohio, S. Yamada et al., "Alfa–Amination". . . p. 537, col 1.
Tetrahedron Letters, No. 51, 1965, Oxford F. Minisci et al. "Homolytic amination of aromatic" . . . , pp. 4663–4667.
J. Am. Chem. Soc. 1992, 114, pp. 9237–9238 "Direct Coupling of Aniline and Nitrobenzene: . . . ".
J. Org. Chem. 1993, 58, pp. 6883–6888 "Amination of Nitrobenzene via Nucleophilic Aromatic Substitution for Hydrogen: . . . ".
J. Org. Chem. 1986, 51, pp. 5039–5040 "Direct Amination of Nitrobenzenes by Vicarious Nucleophilic Substitution".
J. Org. Chem. 1988, 53, pp. 3978–3982 "Alkylaminonitrobenzenes by Vicarious Nucleophilic Amination with 4–(Alkylamino)–1,2,4–triazoles".
J. Org. Chem. 1992, 57, pp. 4784–4785, "Amination of Nitroarenes with Sulfenamides via Vicarious Nucleophilic Substitution of Hydrogen".
Price, C. C. et al. Organic Synthesis, Collective Vol. III pp. 664–665 (1955).

*Primary Examiner*—Richard L. Raymond
*Attorney, Agent, or Firm*—Birch, Stewart, Kolasch Birch

[57] ABSTRACT

A process for preparing a nitroaniline derivative comprising a step of reacting an aromatic nitro compound with an O-alkylhydroxylamine or a salt thereof in the presence of a base and optionally a metallic catalyst, which process is industrially advantageous since it provides the nitroaniline derivative from the aromatic nitro compound in a high yield in one step, and the aminating agent used can be obtained from hydroxylamine at a relatively low cost.

19 Claims, No Drawings

PROCESS FOR PREPARING NITROANILINE DERIVATIVES

FIELD OF THE INVENTION

The present invention relates to a process for preparing a nitroaniline derivative by direct amination of an aromatic nitro compound using an O-alkylhydroxylamine or a salt thereof.

DESCRIPTION OF THE PRIOR ART

Nitroaniline derivatives are hitherto known to be precursors of aromatic diamines and hence very important compounds as raw materials and intermediates for medicines, agrochemicals, dyes, additives, etc. It is long known to prepare nitroanilines industrially, for example, by the nitration of acetanilide derivatives, or the amination of halogenated or hydroxylated nitrobenzene derivatives. However, the processes-have many problems that they require many reaction steps, severe reaction conditions and the treatment of waste acids.

The direct amination of aromatic nitro compounds which is the simplest process for preparing the nitroaniline derivatives is being studied in various ways. However, it is not industrially practical in terms of generality and cost. For examples, there are known the process in which 1-nitronaphthalene is directly aminated with hydroxylamine in the presence of potassium hydroxide to obtain 4-nitro-1-naphthylamine (see Org. Synth., Coil. Vol. 3, 664 (1955)), the process in which nitrobenzene couples with aniline in the presence of tetramethylammonium hydroxide to obtain 4-nitrodiphenylamine and 4-nitrosodiphenylamine (see J. Am. Chem. Soc., Vol. 114, 9237 (1992) and U.S. Pat. No. 5,117,063), the process in which nitrobenzenes react with 4-amino-1,2,4-triazole in the presence of a base (see J. Org. Chem., Vol. 51, 5039 (1986) and Vol. 53, 3978 (1988)), and the process in which nitrobenzenes react with sulfenamide in the presence of a base (see J. Org. Chem., Vol. 57, 4784 (1982)).

However, the first two processes are disadvantageous in that raw materials are limited to the compounds described and hence they cannot be used as general processes. The other processes use the very expensive aminating agents which have high molecular weights and are required in the amount of more than one equivalent, so that they have to be recovered and reused. Therefore, the processes are difficult to be practically used in the industries.

The process in which nitrobenzene reacts with benzamide in the presence of tetramethylammonium hydroxide is also known (see J. Org. Chem., Vol. 58, 6883(1993)). However, the process has many problems in the practical use that, since an amide is formed as an intermediate in the process, it should be hydrolyzed to obtain an amine, and that benzamide must be recovered and reused.

In addition, the para position to nitro groups in an aromatic ring is aminated predominantly in any of the processes mentioned. Therefore it is extremely difficult to prepare ortho-nitroaniline predominantly by the direct amination.

SUMMARY OF THE INVENTION

It is an object of the present invention to provide a process for preparing industrially advantageously a nitroaniline derivative by direct amination of an aromatic nitro compound.

It has been found that, when an O-alkylhydroxylamine which can be prepared readily from hydroxylamine at a comparatively low cost is used as an aminating agent, the desired nitroaniline derivative can be easily obtained, the nitroaniline derivative in which the ortho position to the nitro group in an aromatic ring is aminated predominantly can be obtained, and that the use of a metallic catalyst, particularly a copper catalyst, considerably increases the yield of the nitroaniline derivative.

Accordingly, the present invention provides a process for preparing a nitroaniline derivative of the general formula:

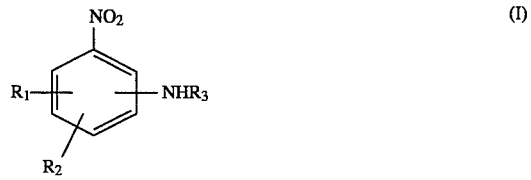

wherein $R_1$ and $R_2$ independently represent a hydrogen atom, a halogen atom, a cyano group, a nitro group, an aryl group, a di-lower alkylamino group, a lower alkyl group optionally substituted with halogen atoms or lower alkoxyl groups, a lower alkoxyl group optionally substituted with halogen atoms, an aryloxy group, a lower alkylmercapto group, an arylmercapto group, a lower alkylsulfonyl group, an arylsulfonyl group, a lower alkyl sulfonate group, or an alkenyl group optionally substituted with lower alkyl groups or aryl groups, or $R_1$ and $R_2$ may form together a cycloalkyl group, an —O—$(CX_2)_n$—O— group, a —$CX_2$—O—$CX_2$— group wherein X represents a hydrogen atom or a halogen atom and n is 1 or 2, or a condensed aromatic carbon ring when $R_1$ and $R_2$ are positioned at the ortho positions in an aromatic ring to each other; and $R_3$ represents a hydrogen atom, a lower alkyl group, an arylmethyl group or a cycloalkyl group having 3 to 8 carbon atoms, comprising a step of reacting an aromatic nitro compound of the general formula:

wherein $R_1$ and $R_2$ are the same as defined above, with an O-alkylhydroxylamine of the general formula:

$$R_3NHOR_4 \quad (III)$$

wherein $R_3$ is the same as defined above and $R_4$ represents a lower alkyl group or a benzyl group, or a salt thereof in the presence of a base or in the presence of a base and a metallic catalyst.

DETAILED DESCRIPTION OF THE INVENTION

In the present invention, the term "lower alkyl group" means a linear or branched alkyl group containing 1 to 4 carbon atoms, the term "lower alkoxy group" a linear or branched alkoxy group containing 1 to 4 carbon atoms, and the term "aryl" a phenylene group optionally substituted with a halogen atom, a linear or branched alkyl group containing 1 to 4 carbon atoms or a linear or branched alkoxy group containing 1 to 4 carbon atoms.

Examples of the aromatic nitro compound of the general formula (ll) used as a starting substance include nitrobenzene, o-chloronitrobenzene, m-chloronitrobenzene, p-chloronitrobenzene, o-bromonitrobenzene, m-bromonitrobenzene, p-bromonitrobenzene, m-fluoronitrobenzene, o-nitrobenzonitrile, m-nitrobenzonitrile, p-nitrobenzonitrile, 1,3-dinitrobenzene, 2-nitrobiphenyl, 3-nitrobiphenyl, 4-nitrobiphenyl, N,N-dimethyl-3-nitroaniline, o-tert.-butylnitrobenzene, m-tert.-butylnitrobenzene, p-tert.-butylnitrobenzene,-o-trifluoromethylnitrobenzene, m-trifluoromethylnitrobenzene, p-trifluoromethylnitrobenzene, o-nitroanisole, m-nitroanisole, p-nitroanisole, 1,2-dimethoxy-4-nitrobenzene, o-trifluoromethoxynitrobenzene, m-trifluoromethoxynitrobenzene, p-trifluoromethoxynitrobenzene, 4-nitrothioanisole, 4-nitrodiphenylsulfide, 4-nitrophenylsulfone, methyl 3-nitrobenzenesulfonate, methyl 4-nitrobenzenesulfonate, 4-nitrostilbene, 1-nitronaphthalene, 2-nitronaphthalene, 3,4-methylenedioxynitrobenzene, 5-nitro-1,1,3,3-tetrafluoro-1,3-dihydroisobenzofuran, etc.

Examples of the O-alkylhydroxylamine represented by the formula (lll) include O-methylhydroxylamine, O-ethylhydroxylamine, O-tert.-butylhydroxylamine, O-n-butylhydroxylamine, N,O-dimethylhydroxylamine, O-benzylhydroxylamine, N-cyclohexyl-O-methylhydroxylamine, N-benzyl-O-methylhydroxylamine, etc.

These O-alkyl hydroxylamine may be used as such or in the form of salts thereof, for example, inorganic salts such as hydrochlorides or sulfate. It may-be usually used in an amount of from 0.8 to 2 moles, preferably from 1 to 1.5 moles per mole of the aromatic nitro compound.

The reaction may be carried out in the presence of a base. The kinds of bases are not particularly restricted and include, for example, alkali metal hydroxides, alkali metal hydrides, alkali metal amides, alkali metal alkoxides, etc. Specific examples of the bases are sodium hydroxide, potassium hydroxide, sodium hydride, sodium amide, lithium amide, lithium diisopropylamide, sodium methoxide, sodium ethoxide, potassium tert.-butoxide, etc.

The base is usually used in an amount of from 1 to 6 moles, preferably 2 to 5 moles per mole of the O-alkylhydroxylamine or the salt thereof.

The reaction according to the present invention may be carried out in the absence of a catalyst. But the use of a metallic catalyst increases the yield of the nitroaniline derivative.

Examples of the metallic catalyst to be used for such purpose include various metals such as copper, manganese, iron, nickel, cobalt, silver, chromium and zinc, and compounds thereof. The metal compounds include halides, oxides, sulfides, hydroxides, carboxylates, nitrates, sulfates, carbonates, sulfonates, phosphates, thiocyanates, chromates, perchlorates, alkoxides, cyanides and acetylacetonates of these metals.

Specific examples of the metallic catalysts are copper, cuprous chloride, cupric chloride, cuprous bromide, cupric bromide, cuprous iodide, cuprous oxide, cupric oxide, copper sulfide, copper acetate, copper nitrate, copper sulfate, copper carbonate, copper hydroxide, copper cyanide, copper acetylacetonate, copper phosphate, copper thiocyanate, copper chromate, copper perchlorate, copper methoxide, manganese chloride, manganese bromide, manganese acetate, manganese carbonate, manganese nitrate, manganese sulfate, manganese acetylacetonate, zinc chloride, cobalt chloride, nickel chloride, ferrous chloride, ferric chloride, iron oxides, silver oxide, etc. The copper compounds-and the manganese compounds, particularly the copper compounds, are preferred. The halides, carboxylates, nitrate and acetylacetonate of copper are particularly preferred. These metallic compounds which contain water of crystallization can also be used as the catalysts without problems.

When the metallic catalyst is used, it may be usually used in an amount of not more than 1.5 mole, not more than 0.2 mole in many cases, per mole of the aromatic nitro compound used as the starting material. The lower limit is not limited, but is usually 0.005 mole, preferably 0.01 mole, per mole of the aromatic nitro compound in order to ensure the effect of the use of the metallic catalyst.

The reaction according to the present invention is usually carried out in the presence of a solvent. Examples of the solvent are aprotic polar solvents such as N,N-dimethylformamide, dimethyl sulfoxide; etheric solvents such as ethylene glycol dimethyl ether, diethylene glycol dimethyl ether, 1,4-dioxane or tetrahydrofuran; aromatic solvents such as benzene, toluene, xylene or chlorobenzene; aliphatic hydrocarbon solvents such as n-hexane, n-heptane or cyclohexane; alcoholic solvents such as tert.-butanol; liquid ammonia,etc. They may be used in admixture. In the reaction system in which the metallic catalyst is not used, aromatic hydrocarbon solvents such as benzene or toluene, or aliphatic hydrocarbon solvents such as n-hexane, n-heptane, cyclohexane are preferably used.

The solvent is used in an amount of from 5 to 100 times by weight of the aromatic nitro compound used as the starting substance.

In the reaction according to the present invention, the aromatic nitro compound may be used as both a starting substance and a solvent, without using another solvent.

The reaction temperature is usually in the range of from −40° to 100° C., preferably from 0° to 50° C.

After the reaction is completed, the products can be easily isolated and purified from the reaction mixture by any of conventional procedures, for example, distillation, extraction, recrystallization or various kinds of chromatography.

EXAMPLES

The present invention will be illustrated by Examples, but is not limited thereto.

EXAMPLE 1

246 mg (2 mmol) of nitrobenzene and 118 mg (2.5 mmol) of O-methylhydroxylamine were dissolved in 3 ml of N,N-dimethylformamide. The mixture was added dropwise to 8 ml of N,N-dimethylformamide containing 673 mg (6 mmol) of potassium tert.-butoxide at 27° C. during 10 minutes. Then the reaction mixture changed to red immediately, and the internal temperature was elevated to 33° C. by exothermic reaction. After the completion of the dropwise addition, the reaction mixture was stirred at 27° C. for 1 hour. An aqueous saturated ammonium chloride solution was then added to the reaction mixture, followed by extraction with methylene chloride.

Analysis of the extract by gas chromatography indicated the following results.

Conversion of nitrobenzene: 75%

Yield of o-nitroaniline: 39% (Selectivity: 52%)

Yield of p-nitroaniline: 21% (Selectivity: 28%)

EXAMPLE 2

246 mg (2 mmol) of nitrobenzene and 118 mg (2.5 mmol) of O-methylhydroxylamine were dissolved in 3 ml of N,N-dimethylformamide. The mixture was added dropwise to 7 ml of N,N-dimethylformamide containing 673 mg (6 mmol) of potassium tert.-butoxide and 38 mg (0.2 mmol) of cuprous iodide at 25° C. during 5 minutes. After the completion of the dropwise addition, the reaction mixture was stirred at 25° C. for 1 hour. An aqueous saturated ammonium chloride solution was then added to the reaction mixture, followed by the extraction with methylene chloride.

Analysis of the extract by gas chromatography indicated the following results.

Conversion of nitrobenzene: 96%
Yield of o-nitroaniline: 66% (Selectivity: 69%)
Yield of p-nitroaniline:. 27% (Selectivity: 28%)

EXAMPLE 3

246 mg (2 mmol) of nitrobenzene and 118 mg (2.5 mmol) of O-methylhydroxylamine were dissolved in 3 ml of N,N-dimethylformamide. The mixture was added dropwise to 7 ml of N,N-dimethylformamide containing 673 mg (6 mmol) of potassium tert.-butoxide and 3.8 mg (0.02 mmol) of cuprous iodide at 25° C. during 5 minutes. After the completion of the dropwise addition, the reaction mixture was stirred at 25° C. for 1 hour. An aqueous saturated ammonium chloride solution was then added to the reaction mixture, followed by the extraction with methylene chloride.

Analysis of the extract by gas chromatography indicated the following results.

Conversion of nitrobenzene: 95%
Yield of o-nitroaniline: 60% (Selectivity: 63%)
Yield of p-nitroaniline: 23% (Selectivity: 24%)

EXAMPLE 4

246 mg (2 mmol) of nitrobenzene and 215 mg (2.5 mmol) of O-methylhydroxylamine hydrochloride were dissolved in 3 ml of N,N-dimethylformamide. The mixture was added dropwise to 8 ml of N,N-dimethylformamide containing 954 mg (8.5 mmol) of potassium tert.-butoxide at 27° C. during 10 minutes. After the completion of the dropwise addition, the reaction mixture was stirred at 27° C. for 1 hour. An aqueous saturated ammonium chloride solution was then added to the reaction mixture, followed by the extraction with methylene chloride.

Analysis of the extract by gas chromatography indicated the following results.

Conversion of nitrobenzene: 72%
Yield of o-nitroaniline: 40% (Selectivity: 56%)
Yield of p-nitroaniline: 15% (Selectivity: 21%)

EXAMPLE 5

246 mg (2 mmol) of nitrobenzene and 215 mg (2.5 mmol) of O-methylhydroxylamine hydrochloride were dissolved in 3 ml of N,N-dimethylformamide. The mixture was added dropwise to 7 ml of N,N-dimethylformamide containing 954 mg (8.5 mmol) of potassium tert.-butoxide and 21 mg (0.2 mmol) of cuprous chloride (95%) at 25° C. during 5 minutes. After the completion of the dropwise addition, the reaction mixture was stirred at 25° C. for 1 hour. An aqueous saturated ammonium chloride solution was then added to the reaction mixture, followed by the extraction with methylene chloride.

Analysis of the extract by gas chromatography indicated the following results,

Conversion of nitrobenzene: 95%
Yield of o-nitroaniline: 64% (Selectivity: 67%)
Yield of p-nitroaniline: 28% (Selectivity: 29%)

EXAMPLE 6

Example 4 was repeated except that 244 mg (2.5 mmol) of O-ethylhydroxylamine hydrochloride was used in place of O-methylhydroxylamine hydrochloride and the following results were obtained, Conversion of nitrobenzene: 57%
Yield of o-nitroaniline: 23% (Selectivity: 40%)
Yield of p-nitroaniline: 15% (Selectivity: 26%)

EXAMPLE 7

Example 5 was repeated except that 244 mg (2,5 mmol) of O-ethylhydroxylamine hydrochloride was used in place of O-methylhydroxylamine hydrochloride and the following results were obtained.

Conversion of nitrobenzene: 86%
Yield of o-nitroaniline: 46% (Selectivity: 53%)
Yield of p-nitroaniline: 21% (Selectivity: 24%)

EXAMPLE 8

Example 5 was repeated except that 314 mg (2.5 mmol) of O-tert.-butylhydroxylamine hydrochloride was used in place of O-methylhydroxylamine hydrochloride and the following results were obtained.

Conversion of nitrobenzene: 77%
Yield of o-nitroaniline: 8% ( Selectivity: 10% )
Yield of p-nitroaniline: 23% (Selectivity: 30%)

EXAMPLE 9

Example 5 was repeated except that 399 mg (2.5 mmol) of O-benzylhydroxylamine hydrochloride was used in place of O-methylhydroxylamine hydrochloride and the following results were obtained.

Conversion of nitrobenzene: 68%
Yield of o-nitroaniline: 31% (Selectivity: 46%)
Yield of p-nitroaniline: 10% (Selectivity: 15%)

EXAMPLE 10

Example 4 was repeated except that 244 mg (2.5 mmol) of N,O-dimethylhydroxylamine hydrochloride was used in place of O-methylhydroxylamine hydrochloride. Thereafter, the product was isolated by silica gel thin layer chromatography (eluent: ethyl acetate/n-hexane=⅕ by volume).

Conversion of nitrobenzene: 52%
Yield of N-methyl-4-nitroaniline: 18% (Selectivity: 34%)

EXAMPLE 11

382 mg (2 mmol) of m-trifluoromethylnitrobenzene and 118 mg (2.5 mmol) of O-methylhydroxylamine were dissolved in 3 ml of N,N-dimethylformamide. The mixture was added dropwise to 7 ml of N,N-dimethylformamide containing 673 mg (6 mmol) of potassium tert.-butoxide and 21 mg (0.2 mmol) of cuprous chloride (95%) at 25° C. during 5 minutes. After the completion of the dropwise addition, the reaction mixture was stirred at 25° C. for 1 hour. An aqueous saturated ammonium chloride solution was then added to the reaction mixture, followed by the extraction with methylene chloride.

Analysis of the extract by gas chromatography indicated the following results given in Table 1.

EXAMPLES 12 TO 31 AND COMPARATIVE EXAMPLE 1

Example 11 was repeated except that each of the metallic catalysts shown in Table 1 was used in place of cuprous chloride. The results are given in Table 1.

TABLE 1

| Ex. No. | Catalyst | Conv. (%) | Yield (%) | Select. (%) | Isomer Ratio (%) | | |
|---|---|---|---|---|---|---|---|
| | | | | | 2,4- | 6,2- | 4,2- |
| 11 | CuCl | 98 | 93 | 95 | 50 | 26 | 24 |
| 12 | CuI | 96 | 89 | 93 | 50 | 27 | 23 |
| 13 | CuBr | 98 | 91 | 93 | 49 | 28 | 23 |
| 14 | $Cu(acac)_2$ | 92 | 83 | 90 | 50 | 27 | 23 |
| 15 | $CuCl_2$ | 95 | 83 | 87 | 49 | 29 | 22 |
| 16 | $Cu(NO_3)_2.3H_2O$ | 99 | 90 | 91 | 49 | 27 | 24 |
| 17 | $Cu(OAc)_2.H_2O$ | 99 | 95 | 96 | 50 | 27 | 23 |
| 18 | CuCN | 84 | 52 | 62 | 50 | 28 | 22 |
| 19 | $Cu(OH)_2$ | 81 | 41 | 51 | 50 | 29 | 21 |
| 20 | $CuSO_4$ | 78 | 37 | 48 | 48 | 30 | 22 |
| 21 | Cu | 75 | 30 | 40 | 48 | 31 | 21 |
| 22 | $MnCl_2.4H_2O$ | 93 | 57 | 61 | 47 | 29 | 24 |
| 23 | $Mn(OAc)_2.4H_2O$ | 90 | 40 | 44 | 50 | 26 | 24 |
| 24 | $Mn(acac)_3$ | 83 | 38 | 45 | 50 | 24 | 26 |
| 25 | $\gamma\text{-}Fe_2O_3$ | 72 | 29 | 40 | 48 | 31 | 21 |
| 26 | $FeCl_3$ | 73 | 29 | 40 | 51 | 27 | 22 |
| 27 | $FeCl_2.nH_2O$ | 75 | 32 | 43 | 48 | 31 | 21 |
| 28 | $NiCl_2$ | 75 | 28 | 38 | 54 | 25 | 21 |
| 29 | $Ag_2O$ | 79 | 31 | 40 | 48 | 30 | 22 |
| 30 | $CrCl_3.6H_2O$ | 73 | 30 | 50 | 48 | 32 | 20 |
| 31 | $ZnCl_2$ | 75 | 35 | 46 | 51 | 28 | 21 |
| Comp. 1 | none | 71 | 26 | 36 | 48 | 31 | 21 |

Notes:
2,4-: 2-nitro-4-trifluoromethylaniline
6,2-: 6-nitro-2-trifluoromethylaniline
4,2-: 4-nitro-2-trifluoromethylaniline

EXAMPLE 32

Example 11 was repeated except that sodium hydroxide (6 mmol) was used in place of potassium tert.-butoxide and the following results were obtained.

Conversion of m-trifluoromethylnitrobenzene: 100%

Yield of 2-nitro-4-trifluoromethylaniline: 55%

Yield of 6-nitro-2-trifluoromethylaniline: 11%

Yield of 4-nitro-2-trifluoromethylaniline: 16%

EXAMPLE 33

Example 11 was repeated except that 314 mg (2.5 mmol) of O-tert.-butylhydroxylamine hydrochloride was used in place of O-methylhydroxylamine and that potassium tert.-butoxide was used in an amount of 954 mg (8.5 mmol). The following results were obtained.

Conversion of m-trifluoromethylnitrobenzene: 89%

Yield of 2-nitro-4-trifluoromethylaniline: 15% (Selectivity 17%)

Yield of 6-nitro-2-trifluoromethylaniline: 4% (Selectivity 4%)

Yield of 4-nitro-2-trifluoromethylaniline: 32% (Selectivity 36%)

EXAMPLE 34

315 mg (2 mmol) of m-chloronitrobenzene and 118 mg (2.5 mmol) of O-methylhydroxylamine were dissolved in 3 ml of N,N-dimethylformamide. The mixture was added dropwise to 7 ml of N,N-dimethylformamide containing 673 mg (6 mmol) of potassium tert.-butoxide and 21 mg (0.2 mmol) of cuprous chloride (95%) at 25° C. during 5 minutes. After the completion of the dropwise addition, the reaction mixture was stirred at 25° C. for 1 hour. An aqueous saturated ammonium chloride solution was then added to the reaction mixture, followed by the extraction with methylene chloride.

After the resulting organic layer was dried over anhydrous magnesium sulfate and the solvent was distilled off, products were isolated by silica gel thin layer chromatography (eluent: ethyl acetate/n-hexane=⅕ by volume). The following results were obtained.

Conversion of m-chloronitrobenzene: 100%

Yield of 4-chloro-2-nitroaniline: 15%

Yield of 2-chloro-6-nitroaniline: 41%

Yield of 2-chloro-4-nitroaniline: 29%

EXAMPLE 35

Example 34 was repeated except that m-nitroanisole (2 mmol) was used in place of m-chloronitrobenzene. The following results were obtained.

Conversion of m-nitroanisole: 96%

Yield of 4-methoxy-2-nitroaniline: 14% (Selectivity 15%)

Yield of 2-methoxy-6-nitroaniline:: 56% (Selectivity 59%)

Yield of: 2-methoxy-4-nitroaniline 24% (Selectivity 25%)

EXAMPLE 36

Example 35 was repeated except that cuprous chloride was not used and the following results were obtained.

Conversion of m-nitroanisole: 83%

Yield of 4-methoxy-2-nitroaniline: 9% (Selectivity 10%)

Yield of 2-methoxy-6-nitroaniline: 34% (Selectivity 41%)

Yield of 2-methoxy-4-nitroaniline: 14% (Selectivity 17%)

EXAMPLE 37

Example 34 was repeated except that N,N-dimethyl-3-nitroaniline (2 mmol) was used in place of m-chloronitrobenzene. The following results were obtained.

Conversion of N,N-dimethyl-3-nitroaniline: 100%

Yield of $N^4,N^4$-dimethyl-2-nitro-p-phenylenediamine: 10%

Yield of $N^1,N^1$-dimethyl-3-nitro-o-phenylenediamine: 75%

Yield of $N^2,N^2$-dimethyl-4-nitro-o-phenylenediamine: 15%

EXAMPLE 38

Example 37 was repeated except that cuprous chloride was not used and the following results were obtained.

Conversion of N,N-dimethyl-3-nitroaniline: 68%

Yield of $N^4,N^4$-dimethyl-2-nitro-p-phenylenediamine: 7% (Selectivity 10%)

Yield of $N^1,N^1$-dimethyl-3-nitro-o-phenylenediamine: 47% (Selectivity 70%)

Yield of $N^2,N^2$-dimethyl-4-nitro-o-phenylenediamine: 11% (Selectivity 16%)

The physical properties of $N^1$, $N^1$-dimethyl-3-nitro-o-phenylenediamine were as follows:

$^1$H NMR spectra (CDCl$_3$): δ2.66 (s, 6H), 6.61 (dd, 1H, J=7.59 Hz, 8.91 Hz), 6.69 (br. s, 2H), 7.21 (dd, 1H, J=1.32 Hz, 7.59 Hz), 7.88 (dd, 1H, J=1.32 Hz, 8.91 Hz)

Mass spectra: m/z 181(M+), 162, 147, 145, 133, 119, 105, 92, 78, 65, 52, 42

EXAMPLES 39 to 48

Example 34 was repeated except that 2 mmol of p-trifluoromethylnitrobenzene (Example 40), p-chloronitrobenzene (Example 42), p-nitroanisole (Example 44), p-nitrophenyl phenyl ether (Example 46) or 4-nitrothioanisole (Example 48) was used, respectively, in place of m-chloronitrobenzene.

The above reactions were repeated except that cuprous chloride was not used (Examples 39, 41, 43, 45 and 47). The results were shown in Table 2.

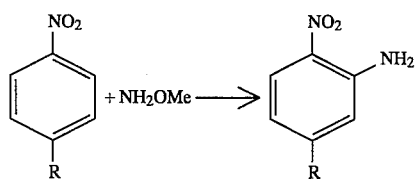

TABLE 2

| Example No. | R | Cat. | Conv. (%) | Yield (%) |
|---|---|---|---|---|
| 39 | CF$_3$ | none | 90 | 28 |
| 40 | CF$_3$ | CuCl | 100 | 76 |
| 41 | Cl | none | 97 | 39 |
| 42 | Cl | CuCl | 100 | 86 |

TABLE 2-continued

| Example No. | R | Cat. | Conv. (%) | Yield (%) |
|---|---|---|---|---|
| 43 | OMe | none | 61 | 41 |
| 44 | OMe | CuCl | 84 | 69 |
| 45 | OPh | none | 100 | 42 |
| 46 | OPh | CuCl | 100 | 70 |
| 47 | SMe | none | 78 | 65 |
| 48 | SMe | CuCl | 95 | 92 |

The physical properties of 2-nitro-5-phenoxyaniline obtained in Examples 45 and 46 were as follows:

$^1$H NMR spectra (CDCl$_3$):

δ6.14 (br. s, 2H), 6.16 (d, 1H, J=2.63 Hz), 6.33 (dd, 1H, J=2.63 Hz, 9.57 Hz), 7.07–7.45 (m, 5H), 8.10 (d, 1H, J=9.57 Hz)

Mass spectra:

m/z 230(M+), 200, 184, 156, 129, 115, 61, 77, 51

EXAMPLE 49

Example 34 was repeated except that 2-nitrobiphenyl (2 mmol) was used in place of m-chlorobenzene, the reaction time was 30 minutes, and that cuprous chloride was not used. The following result was obtained.

Conversion of 2-nitrobiphenyl: 68%

Yield of 2-nitro-3-biphenylamine: 31% (selectivity: 46%)

The physical properties of 2-nitro-3-biphenylamine were as follows:

$^1$H NMR spectra (CDCl$_3$):

δ5.03 (br. s, 2H), 6.65 (dd, 1H, J=1.32 Hz, 7.59 Hz), 6.76 (dd, 1H, J=1.32 Hz, 8.24 Hz), 7.21–7.41 (m, 6H)

Mass spectra:

m/z 214(M+), 197, 185, 167, 157, 139, 130, 115, 91, 77, 63, 51, 39

EXAMPLE 50

Example 34 was repeated except that 2-nitrobiphenyl (2 mmol) was used in place of m-chloronitrobenzene, and the reaction time was 10 minutes. The following results were obtained.

Conversion of 2-nitrobiphenyl: 90%

Yield of 2-nitro-3-biphenylamine: 60% (selectivity: 67%)

Yield of 2-nitro-5-biphenylamine: 26% (selectivity: 29%)

The physical properties of 2-nitro-5-biphenylamine were as follows:

$^1$H NMR spectra (CDCl$_3$):

δ4.64 (br. s, 2H), 6.49 (d, 1H, J=2.64 Hz), 6.60 (dd, 1H, J=2.64 Hz, 8.91 Hz), 7.23–7.39 (m, 5H), 7.91 (d, 1H, J=8.91 Hz)

Mass spectra:

m/z 214(M+), 197, 185, 167, 158, 139, 130, 63

EXAMPLE 51

Example 34 was repeated except that 5-nitro-1,1,3,3-tetrafluoro-1,3-dihydroisobenzofuran (2 mmol) was used in place of m-chloronitrobenzene, and cuprous iodide (0.2 mmol) was used in place of cuprous chloride. The following results were obtained.

Conversion of 5-nitro-1,1,3,3-tetrafluoro-1,3-dihydroisobenzofuran: 100%

Yield of 4-amino-5-nitro-1,1,3,3-tetrafluoro-1,3-dihydroisobenzofuran: 39%

Yield of 5-amino-6-nitro-1,1,3,3-tetrafluoro-1,3-dihydroisobenzofuran: 9%

The physical properties of 4-amino-5-nitro-1,1,3,3-tetrafluoro-1,3-dihydroisobenzofuran were as follows:

$^1$H NMR spectra (CDCl$_3$):

δ6.56 (br. s, 2H), 6.95 (dd, 1H, J=0.99 Hz, 8.58 Hz), 8.50 (d, 1H, J=8.58 Hz)

Mass spectra:

m/z 252(M+), 233, 222, 206, 186, 174, 166, 138, 88, 75, 62, 52

EXAMPLE 52

Example 34 was repeated except that 1-nitronaphthalene (2 mmol) was used in place of m-chloronitrobenzene. The following results were obtained.

Conversion of 1-nitronaphthalene: 100%

Yield of 1-nitro-2-naphthylamine: 34%

Yield of 4-nitro-1-naphthylamine: 7%

EXAMPLE 53

Example 11 was repeated except that toluene was used as a solvent in place of N,N-dimethylformamide and cuprous chloride was not used. The following results were obtained.

Conversion of m-trifluoromethylnitrobenzene: 96%

Yield of 2-nitro-4-trifluoromethylaniline: 40% (Selectivity 42%)

Yield of 6-nitro-2-trifluoromethylaniline: 35% (Selectivity 36%)

Yield of 4-nitro-2-trifluoromethylaniline: 7% (Selectivity 7%)

EXAMPLE 54

Example 11 was repeated except that n-hexane was used as a solvent in place of N,N-dimethylformamide and cuprous chloride was not used. The following results were obtained.

Conversion of m-trifluoromethylnitrobenzene: 94%

Yield of 2-nitro-4-trifluoromethylaniline: 41% (Selectivity 44%)

Yield of 6-nitro-2-trifluoromethylaniline: 35% (Selectivity 37%)

Yield of 4-nitro-2-trifluoromethylaniline: 8% (Selectivity 9%)

According to the present invention, the nitroaniline derivatives can be easily prepared in a high yield in one step.

The process according to the present invention is industrially advantageous since the O-alkylhydroxylamines or the salts thereof which are used as the aminating agents in the process can be easily obtained from hydroxylamine at a relatively low cost.

The process according to the present invention is very suitable for preparing the ortho phenylenediamine derivatives since the amination according to the present invention takes place at the ortho positions to the nitro groups in the aromatic rings predominantly.

What is claimed is:

1. A process for preparing a nitroaniline derivative of the general formula:

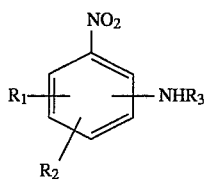

(I)

wherein R$_1$ and R$_2$ independently represent a hydrogen atom, a halogen atom, a cyano group, a nitro group, an aryl group, a di-lower alkylamino group, a lower alkyl group optionally substituted with halogen atoms or lower alkoxyl groups, a lower alkoxyl group optionally substituted with halogen atoms, an aryloxy group, a lower alkylmercapto group, an arylmercapto group, a lower alkylsulfonyl group, an arylsulfonyl group, a lower alkyl sulfonate group, or an alkenyl group optionally substituted with lower alkyl groups or aryl groups, or R$_1$ and R$_2$ may form together a cycloalkyl group, an —O—(CX$_2$)$_n$—O— group, a —CX$_2$—O—CX$_2$— group wherein X represents a hydrogen atom or a halogen atom and n is 1 or 2, or a condensed aromatic carbon ring when R$_1$ and R$_2$ are positioned at the ortho positions in an aromatic ring to each other; and R$_3$ represents a hydrogen atom, a lower alkyl group, an arylmethyl group or a cycloalkyl group having 3 to 8 carbon atoms, comprising a step of reacting an aromatic nitro compound of the general formula:

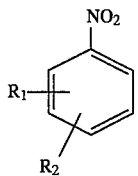

(II)

wherein R$_1$ and R$_2$ are the same as defined above, with an O-alkylhydroxylamine of the general formula:

(III)

wherein R$_3$ are the same as defined above and R$_4$ represents a lower alkyl group or a benzyl group, or a salt thereof in the presence of a base.

2. A process for preparing a nitroaniline derivative as claimed in claim 1 wherein the reaction is carried out in the presence of a metallic catalyst.

3. A process for preparing a nitroaniline derivative as claimed in claim 1 or 2 wherein said O-alkylhydroxylamine is O-methylhydroxylamine, O-ethylhydroxylamine, O-tert.-butylhydroxylamine, O-benzylhydroxylamine, or N,O-dimethylhydroxylamine.

4. A process for preparing a nitroaniline derivative as claimed in claim 1 or 2, wherein said O-alkylhydroxylamine is O-methylhydroxylamine.

5. A process for preparing a nitroaniline derivative as claimed in claim 1 or 2 wherein said salt of the O-alkylhydroxylamine is an inorganic acid salt of O-alkylhydroxylamine.

6. A process for preparing a nitroaniline derivative as claimed in claim 5 wherein said inorganic acid salt is a hydrochloric acid salt.

7. A process for preparing a nitroaniline derivative as claimed in claim 1 or 2 wherein said base is an alkaline metal compound.

8. A process for preparing a nitroaniline derivative as claimed in claim 7 wherein said alkaline metal compound is an alkaline metal alkoxide or an alkaline metal hydroxide.

9. A process for preparing a nitroaniline derivative as claimed in claim 1 or 2 wherein said O-alkylhydroxylamine or the salt thereof is used in an amount of 0.8 to 2 moles per mole of the aromatic nitro compound.

10. A process for preparing a nitroaniline derivative as claimed in claim 1 or 2 wherein said base is used in an amount of 1 to 6 moles per mole of the O-alkylhydroxylamine or the salt thereof.

11. A process for preparing a nitroaniline derivative as claimed in claim 1 or 2 wherein the reaction is carried out in a non-polar solvent.

12. A process for preparing a nitroaniline derivative as claimed in claim 11 wherein the non-polar solvent is an aliphatic hydrocarbon solvent or an aromatic hydrocarbon solvent.

13. A process for preparing a nitroaniline derivative as claimed in claim 12 wherein the aliphatic hydrocarbon solvent is n-hexane, n-heptane or cyclohexane, and the aromatic hydrocarbon solvent is benzene, toluene or xylene.

14. A process for preparing a nitroaniline derivative as claimed in claim 2 wherein the metallic catalyst is copper or a copper compound.

15. A process for preparing a nitroaniline derivative as claimed in claim 14 wherein the copper compound is a halide, a carboxylate, a nitrate or a acetylacetonate of the copper.

16. A process for preparing a nitroaniline derivative as claimed in claim 2 wherein the metallic compound is manganese or a manganese compound.

17. A process for preparing a nitroaniline derivative as claimed in claim 16 wherein the manganese compound is a halide, a carboxylate or a acetylacetonate of the manganese.

18. A process for preparing a nitroaniline derivative as claimed in claim 2 wherein the metallic catalyst is used in an amount of 0.005 to 1.5 moles per mole of the aromatic nitro compound.

19. A process for preparing a nitroaniline derivative as claimed in claim 1 or 2 wherein the reaction is carried out at a temperature of −40° to 100° C.

* * * * *